(12) United States Patent
DiMauro

(10) Patent No.: US 9,707,314 B2
(45) Date of Patent: Jul. 18, 2017

(54) ACRYLIC BONE CEMENT HAVING A DELAYED RELEASE POLYMERIZATION INHIBITOR SUCH AS AN ANTI-OXIDANT FOR INCREASED WORKING TIME

(71) Applicant: DePuy Synthes Products, Inc., Raynham, MA (US)

(72) Inventor: Thomas M. DiMauro, Southboro, MA (US)

(73) Assignee: DePuy Synthes Products, Inc., Raynham, MA (US)

(*) Notice: Subject to any disclaimer, the term of this patent is extended or adjusted under 35 U.S.C. 154(b) by 0 days.

(21) Appl. No.: 14/667,905

(22) Filed: Mar. 25, 2015

(65) Prior Publication Data
US 2015/0273107 A1    Oct. 1, 2015

Related U.S. Application Data

(60) Provisional application No. 61/970,568, filed on Mar. 26, 2014.

(51) Int. Cl.
| | |
|---|---|
| A61L 27/16 | (2006.01) |
| C08L 33/08 | (2006.01) |
| A61L 24/06 | (2006.01) |
| C08L 33/12 | (2006.01) |
| A61L 27/50 | (2006.01) |
| A61L 24/00 | (2006.01) |

(52) U.S. Cl.
CPC ............ *A61L 24/06* (2013.01); *A61L 24/001* (2013.01); *A61L 27/16* (2013.01); *A61L 27/50* (2013.01); *C08L 33/12* (2013.01); *A61L 2430/02* (2013.01)

(58) Field of Classification Search
None
See application file for complete search history.

(56) References Cited

U.S. PATENT DOCUMENTS

| | | | | |
|---|---|---|---|---|
| 3,919,773 | A * | 11/1975 | Freeman | A61K 6/083 433/175 |
| 4,494,535 | A * | 1/1985 | Haig | A61B 17/746 606/67 |
| 4,653,489 | A * | 3/1987 | Tronzo | A61B 17/746 606/304 |
| 4,969,888 | A * | 11/1990 | Scholten | A61B 17/8855 606/60 |
| 5,343,877 | A * | 9/1994 | Park | A61B 17/8802 128/897 |
| 6,348,055 | B1 * | 2/2002 | Preissman | A61B 17/8816 604/264 |
| 6,383,188 | B2 * | 5/2002 | Kuslich | A61B 17/1617 408/158 |
| 6,383,190 | B1 * | 5/2002 | Preissman | A61B 17/8819 606/92 |
| 6,448,315 | B1 * | 9/2002 | Lidgren | A61L 27/16 524/110 |

(Continued)

OTHER PUBLICATIONS

Fujisawa, Kinetic Study of the Radical-scavenging Activity of Vitamin E and Ubiquinone, in vivo, 19, 1005-1012, (2005).

*Primary Examiner* — Peter A Salamon

(57) ABSTRACT

A bone cement formulation having i) a PMMA powder fraction designed for quick reaction and ii) a polymerization inhibitor provided in a delayed release form. This allows the cement to obtain an initial viscosity suitable for injection and a long working time.

19 Claims, 3 Drawing Sheets

(56) References Cited

U.S. PATENT DOCUMENTS

| | | | |
|---|---|---|---|
| 8,360,629 B2 | 1/2013 | Globerman | |
| 8,415,407 B2 * | 4/2013 | Beyar | A61L 24/06 |
| | | | 523/117 |
| 8,449,621 B2 * | 5/2013 | Leonard | A61F 2/30 |
| | | | 623/22.15 |
| 8,546,462 B2 | 10/2013 | Boger | |
| 2002/0068974 A1 * | 6/2002 | Kuslich | A61B 17/68 |
| | | | 623/17.11 |
| 2003/0109883 A1 * | 6/2003 | Matsuzaki | A61B 17/1604 |
| | | | 606/86 R |
| 2005/0256220 A1 * | 11/2005 | Lavergne | A61L 24/0094 |
| | | | 523/115 |
| 2008/0107744 A1 * | 5/2008 | Chu | A61F 2/0036 |
| | | | 424/489 |
| 2009/0169532 A1 * | 7/2009 | Ying | A61L 24/001 |
| | | | 424/93.72 |
| 2009/0305983 A1 * | 12/2009 | Ying | A61L 24/001 |
| | | | 514/8.2 |
| 2010/0168271 A1 * | 7/2010 | Beyar | A61L 24/046 |
| | | | 523/116 |
| 2011/0060373 A1 * | 3/2011 | Russell | A61B 17/0401 |
| | | | 606/304 |
| 2011/0224675 A1 * | 9/2011 | Tofighi | A61B 17/8811 |
| | | | 606/94 |
| 2014/0213688 A1 * | 7/2014 | Bezwada | A61L 27/18 |
| | | | 523/116 |
| 2015/0273107 A1 * | 10/2015 | DiMauro | A61L 24/06 |
| | | | 523/116 |

* cited by examiner

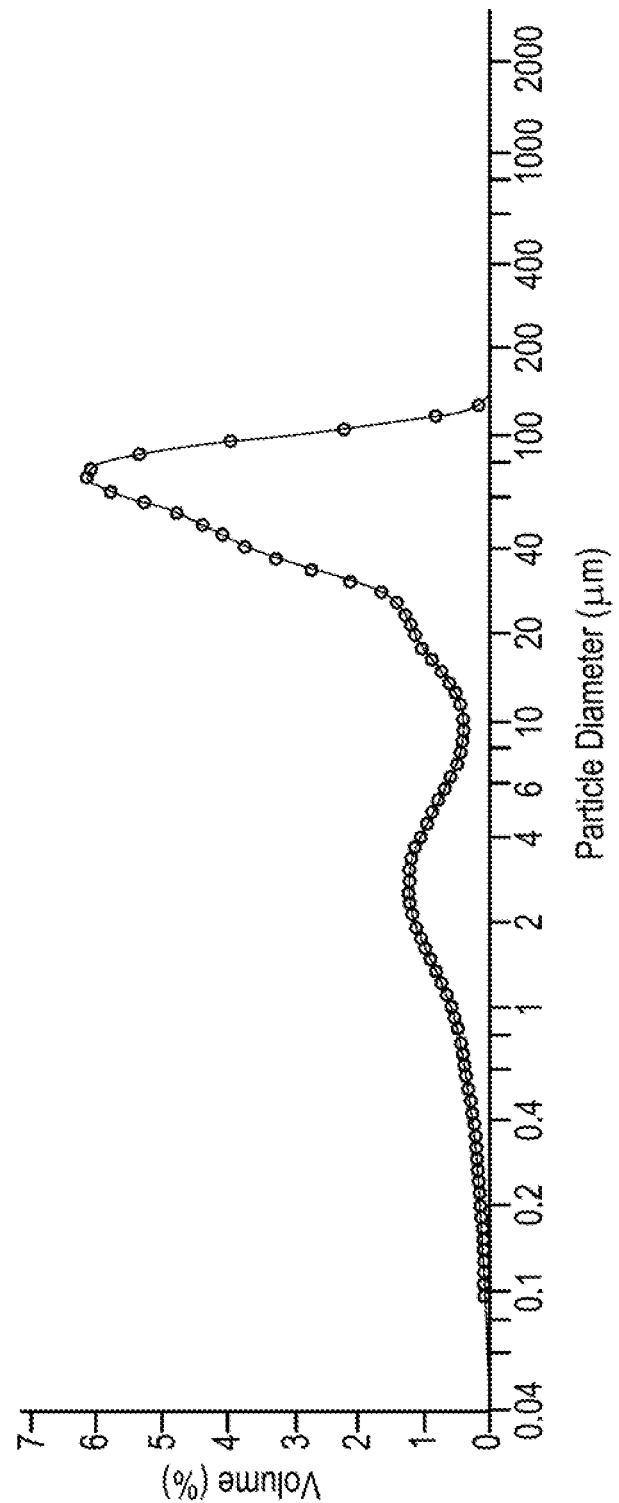

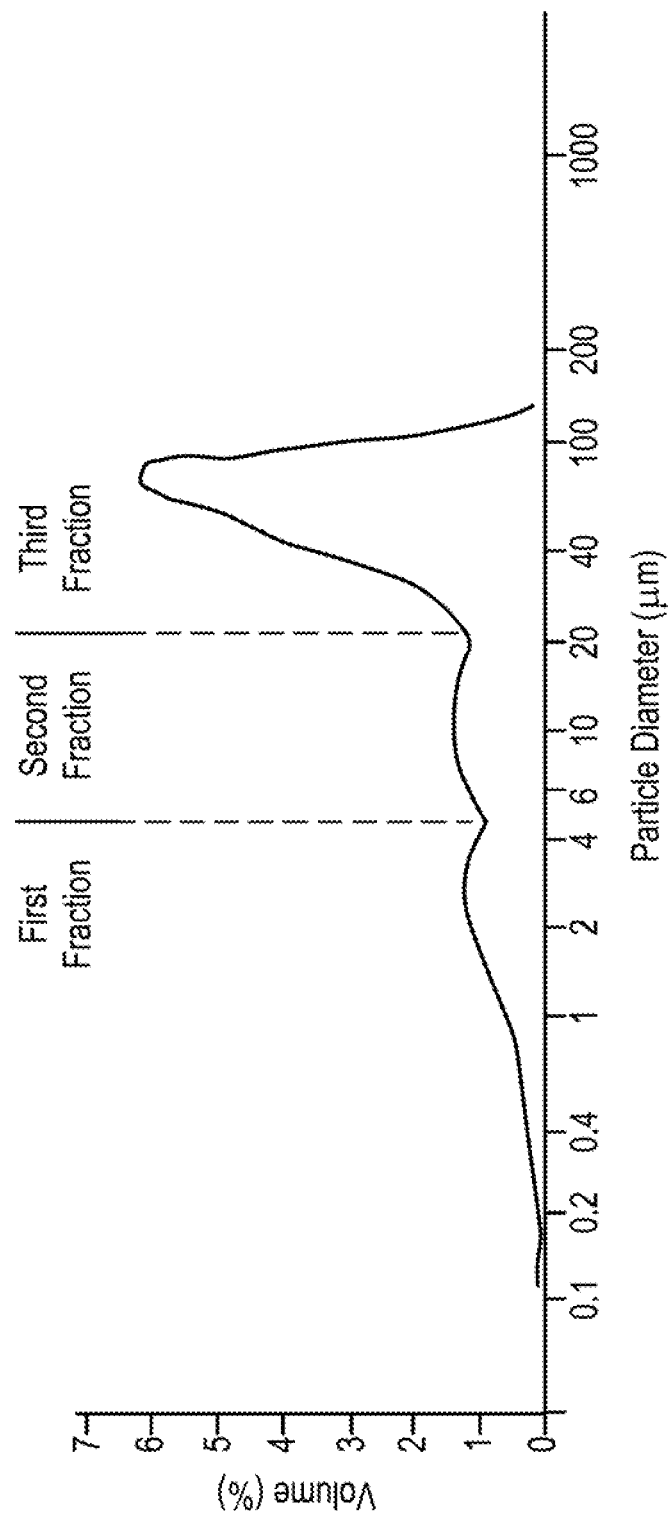

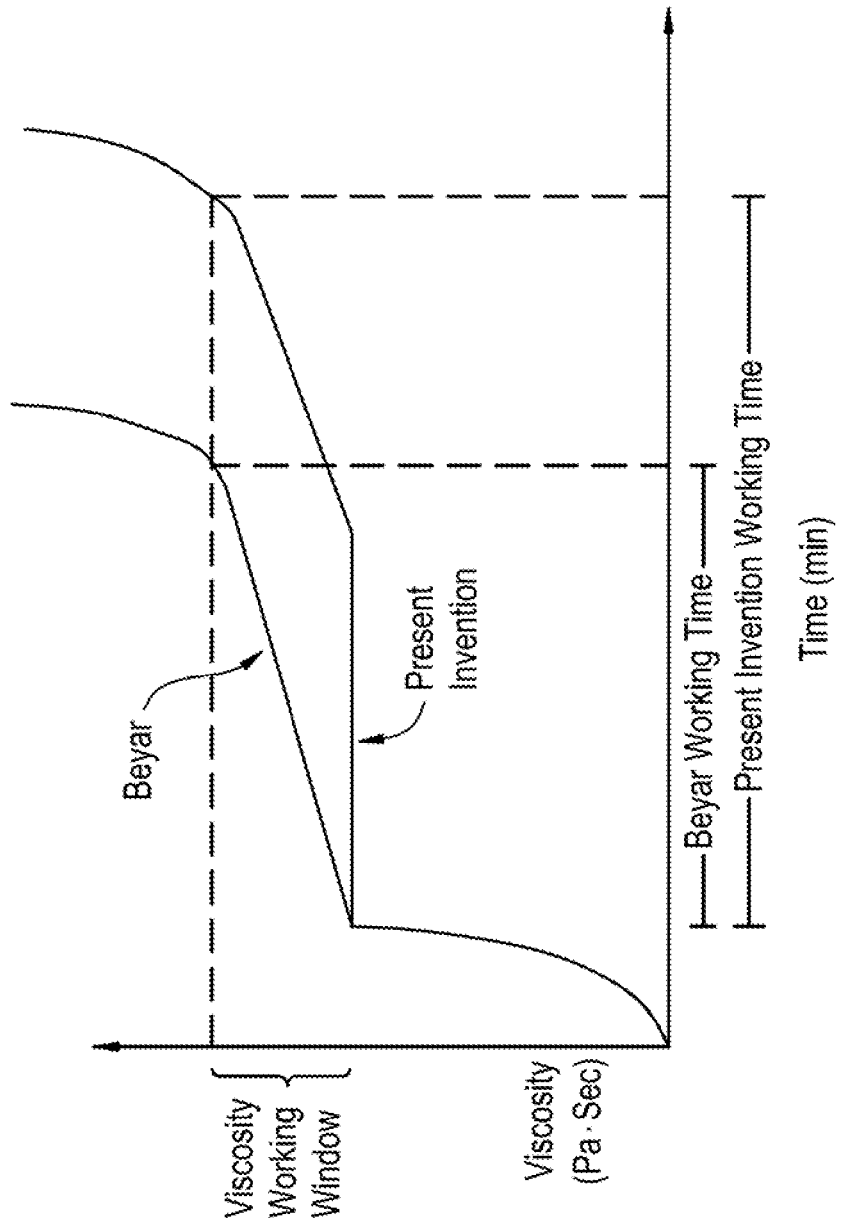

ACRYLIC BONE CEMENT HAVING A DELAYED RELEASE POLYMERIZATION INHIBITOR SUCH AS AN ANTI-OXIDANT FOR INCREASED WORKING TIME

CONTINUING DATA

This non-provisional patent application claims priority from provisional U.S. Ser. No. 61/970,568, filed Mar. 26, 2014, entitled "Acrylic Bone Cement Having a Delayed Release Polymerization Inhibitor such as an Anti-Oxidant For Increased Working Time" (DiMauro).

BACKGROUND OF THE INVENTION

In vertebroplasty, the clinician or surgeon seeks to treat a compression fracture of a vertebra by injecting a curable bone cement such as polymethylmethacrylate (PMMA) into the fracture. In a related procedure called kyphoplasty, the clinician or surgeon first inflates a balloon in the vertebra to create cavity, and then injects the curable bone cement into the cavity. Each procedure is considered to be a form of vertebral body augmentation (VBA).

In the typical PMMA cement, the surgeon mixes a powder component having PMMA particles with a liquid component having MMA monomer. These two components react over the space of about 10 minutes to provide a hardened acrylic cement. The powder and liquids components typically also respectively contain an initiator (such as BPO) and an accelerator (such as DMPT) to adjust the pace of the reaction.

One of the critical areas in VBA is the management of the rapidly curing PMMA cement. The cement typically passes through three phases during its cure: a mixing window (where the viscosity of the cement is too low to safely inject into a fractured vertebral body); a working time window (wherein the viscosity is sufficient high to safely inject but not too thick as to inhibit its injection; and a cure window (where the cement viscosity becomes too high to allow for its further injection). Typically, conventional PMMA cements have working times of less than 10 minutes.

U.S. Patent Application 2010-0168271 (Beyar) discloses PMMA cements engineered to have increased working times. In one embodiment, the PMMA powder component has a bimodal particle size distribution that takes advantage of the high wettability of the smaller particle sized PMMA. See FIG. 1. In use, the smaller particle size portion is wetted quickly by the MMA monomer to provide a quick rise in the viscosity of the cement sufficient to allow the surgeon to quickly begin injecting the cement into the vertebral body. The larger particle size portion is then more slowly wetted by the MMA monomer to provide a more gradual increase in viscosity.

In another embodiment, the PMMA powder component has a bimodal molecular weight distribution that takes advantage of the high wettability of the larger weight PMMA. In practice, the larger molecular weight portion reacts quickly with the MMA monomer to provide a quick rise in the viscosity of the cement sufficient to allow the surgeon to quickly begin injecting the cement into the vertebral body. The smaller weight portion is then slowly wetted by the MMA, inducing a more gradual rise in viscosity.

Despite the significant advance made by Beyar, there remains a need for increased working times in PMMA cements.

SUMMARY OF THE INVENTION

It has been reported in the literature that adding a small amount of an anti-oxidant to a PMMA cement has the effect of delaying the initiation of the increase in viscosity of the cement. Fujisawa, in vivo, 19, 1005-1012, (2005) reports that adding 0.05 mol % Vitamin E to a PMMA system delays the initial rise in viscosity. It appears that adding Vitamin E simply moves the viscosity-time curve to the right without changing its shape. It is hypothesized by the present inventor that the Vitamin E first scavenges reactive oxygen species (thus preventing the free radical reaction and completely delaying any viscosity increase), but is eventually consumed (thereby allowing a subsequent viscosity increase on a time delayed basis).

Therefore, it is contemplated that if such an anti-oxidant were to be added to one of the Beyar cements, wherein the anti-oxidant were to be released at a time intermediate the wetting of the bimodal PMMA fractions, the resulting cement would have a rapid initial increase in viscosity (due to the wetting of a first PMMA fraction); a long working time characterized by essentially no increase in viscosity (due to the subsequent release of the reaction-stemming anti-oxidant until it is consumed), and then a later viscosity-increasing window (due to the eventual wetting of the second PMMA fraction). This would provide the surgeon with valuable additional time to carry out the VBA procedure with the working window.

Therefore, in accordance with the present invention, there is provided (claim 1).

Therefore, in accordance with the present invention, there is provided (claim 11).

DESCRIPTION OF THE FIGURES

FIG. 1 is a prior art graph of a bimodal particle size distribution of a conventional cement that allows for a rapid rise in viscosity followed by a relatively flat viscosity profile.

FIG. 2 is a prophetic graph of a trimodal particle size distribution of a cement of the present invention.

FIG. 3 is a graph of the viscosity profiles of the conventional Beyar cement and that of the present invention.

DETAILED DESCRIPTION OF THE INVENTION

In one preferred embodiment, the powder component of the cement of the present invention comprises:
a) about 60-90 wt % PMMA having a molecular weight of less than 500,000 (preferably between 150,000 and 300,000; more preferably between 270,000 and 300,000);
b) about 1 wt % PMMA having a molecular weight of between about 500,000 and 600,000, and containing the polymerization inhibitor;
c) about 1-4 wt % PMMA (preferably 2-3 wt %) having a molecular weight of between about 600,000 to about 5,000,000 (preferably between about 1,000,000 and about 4,000,000; more preferably between 3,000,000 and 4,000,000);
d) about 5-35 wt % radiopaque agent (preferably, barium sulfate);
e) about 0.1-1 wt % initiator (preferably, benzoyl peroxide)

In another embodiment, the powder component of the cement of the present invention comprises:

a) about 15-30 wt % PMMA having a particle size of less than about 5 um (preferably having a median of about 3 um);
b) about 15-30 wt % PMMA having a particle size of between about 5 and 20 (preferably having a median of about 10 um), and containing the polymerization inhibitor;
c) about 35-65 wt % PMMA (preferably 40-50 wt %) having a particle size of at least about 20 um (preferably having a median of about 100 um);
f) about 5-35 wt % radiopaque agent (preferably, barium sulfate).
g) about 0.1-1 wt % initiator (preferably, benzoyl peroxide)

FIG. 2 is a prophetic graph of a trimodal particle size distribution of a cement of the present invention.

In one embodiment, the liquid component of the cement of the present invention comprises:
a) about 97-99 vol % methyl methacrylate;
b) about 1-3 vol % DmpT
c) about 10-50 ppm hydroquinone (Polymerization Inhibitor)

Preferably, the polymerization inhibitor is an anti-oxidant. More preferably, it is a polyphenol. More preferably, it is present in an amount of between about 0.01 mol % and 1 mol % of the PMMA.

Delayed Release

Any conventional method of providing delayed release of an active agent from a polymeric carrier may be used to delay the release of the polymerization inhibitor (PI) into the powder-liquid system of the present invention. Typically, the carrier is also a polymer, preferably an acrylic polymer powder, such as PMMA. More preferably, it is a PMMA powder having a selected intermediate particle size or molecular weight so that the PI is released after the initial rise in viscosity due to the wetting of a first PMMA fraction with the monomer, but before the wetting of the second fraction of PMMA with the monomer. In some embodiments, the PI is uniformly dispersed in the PMMA powder. In others, it is contained in a carrier shell, such as a microbubble, a micelle or a liposome. In some embodiments wherein the PI is dispersed in a polymer carrier, the carrier is then coated with additional polymer to avoid any burst effect.

(Initiator)

The initiator component of the powder helps start the free radical polymerization of the PMMA. It is typically present in the powder in an amount of 0.1-1 wt %. Typically, it is benzoyl peroxide.

(MMA)

The liquid acrylic monomer undergoes a free radical polymerization to form the PMMA cement. It is typically present in the liquid in an amount of 97-99 vol %. It is typically methylmethacrylate. (MMA).

(Accelerator)

The accelerator component of the liquid speeds the free radical polymerization of the PMMA. It is typically present in the liquid in an amount of 1-3 vol %. Typically, it is DmpT.

(How to Use)

In one prophetic method of using the present invention, the components are mixed until the polymer is wetted by the monomer. Optionally, when wetting is 95 to 100% complete, the mixture has achieved a desired high viscosity, for example 500 Pascal-second or more. Optionally, mixing is complete within 1, 5, 10, 15, 30, 60, 90, 120 or 180 seconds. In a modern medical facility, it can be advantageous to shorten the mixing time in order to reduce the demand on physical facilities and/or medical personnel. A savings of even 1 to 2 minutes with respect to previously available alternatives can be significant. In an exemplary embodiment of the invention, mixing is conducted in a mixing apparatus of the type described in U.S. application Ser. No. 11/428,908, the disclosure of which is fully incorporate herein by reference. After mixing is complete, a working window during which the cement remains viscous but has not fully hardened occurs. During this working window, the polymerization inhibitor contained in the acrylic powder is released, thereby impeding the polymerization reaction and thereby lengthening the working window. The duration of the working window may vary with the exact cement formulation and/or ambient conditions (e.g. temperature and/or humidity). Formulation considerations include, but are not limited to polymer MW (average and/or distribution), polymer bead size, concentrations of non-polymerizing ingredient and polymer:monomer ratio.

In a prophetic embodiment of the invention, a cement characterized by an immediate transition to high viscosity is injected during a working window in a vertebroplasty or kyphoplasty procedure. FIG. 3 is a graph of the viscosity profiles of the conventional Beyar cement and that of the present invention. It is believed that the viscosity profile of the present invention will have a rapid initial increase in viscosity (due to the wetting of a first PMMA fraction); a long working time characterized by essentially no increase in viscosity (due to the subsequent release of the reaction-stemming anti-oxidant until it is consumed), and then a later viscosity-increasing window (due to the subsequent wetting of the second PMMA fraction).

In a prophetic embodiment of the invention, cement with a viscosity profile as described above is useful in vertebral repair, for example in vertebroplasty and/or kyphoplasty procedures. It is believed that the lengthened working window of the present invention will permit a medical practitioner sufficient time to load a high pressure injection device and inject the cement into a desired location. Optionally, an injection needle or cannula is inserted into the body prior to, or concurrent with the mixing so that the window need only be long enough for loading and injection. Exemplary injection systems include the CONFIDENCE injection system marketed by DePuy Synthes Spine of Raynham, Mass.

Optionally, cement injection into a vertebra is under sufficient pressure to move fractured bone, such as fractured plates of a collapsed vertebra. Optionally, injection of viscous cement under high pressure contributes to fracture reduction and/or restoration of vertebral height.

In a prophetic embodiment of the invention, the material (e.g., bone cement) includes processed bone (from human or animals origin) and/or synthetic bone. Optionally, the cement has osteoconductive and/or osteoinductive behavior.

In a prophetic embodiment of the invention, hardening to a hardened condition occurs after the lengthened working window. The cement hardens even if it has not been injected.

Optionally, use of cement which is viscous at the time of injection reduces the risk of material leakage and/or infiltrates into the intravertebral cancellous bone (interdigitaion) and/or reduces the fracture. Reduced leakage optionally contributes to increased likelihood of a positive clinical outcome.

In a prophetic embodiment of the invention, cement is sufficiently viscous to move surrounding tissue as it is injected. Optionally, moving of the surrounding tissue contributes to fracture reduction and/or restoration of vertebral height.

An injected volume of cement may vary, depending upon the type and/or number of orthopedic procedures being performed. The volume injected may be, for example, 2-5 cc for a typical vertebral repair and as high as 8-12 cc or higher for repairs of other types of bones. Other volumes may be appropriate, depending for example, on the volume of space and the desired effect of the injection. In some cases, a large volume of viscous cement is loaded into a delivery device and several vertebrae are repaired in a single medical procedure. Optionally, one or more cannulae or needles are employed to perform multiple procedures.

Viscous cements according to exemplary embodiments of the invention may be delivered at a desired flow rate through standard orthopedic cannulae by applying sufficient pressure. Exemplary average injection rates may be in the range of 0.01 to 0.5 ml/sec, optionally about 0.05, about 0.075 or 0.1 ml/sec or lesser or intermediate or greater average flow rates. Optionally, the flow rate varies significantly during an injection period (e.g., pulse injections). Optionally, the flow rate is controlled manually or using electronic or mechanical circuitry. In an exemplary embodiment of the invention, medical personnel view the cement as it is being injected (e.g. via fluoroscopy) and adjust a flow rate and/or delivery volume based upon observed results. Optionally, the flow rate is adjusted and/or controlled to allow a medical practitioner to evaluate progress of the procedure based upon medical images (e.g. fluoroscopy) acquired during the procedure. In an exemplary embodiment of the invention, the cement is sufficiently viscous that advances into the body when pressure is applied above a threshold and ceases to advance when pressure is reduced below a threshold. Optionally, the threshold varies with one or more of cement viscosity, cannula diameter and cannula length.

It is contemplated that there may be poor mixing of the PI released from the PMMA particle with the liquid phase. If this becomes a concern, then the delivery cannula of the injection device can be vibrated to help achieve better mixing.

What is claimed:

1. A bone cement formulation comprising:
    a) a powder component comprising: i) an acrylic polymer powder, and ii) an initiator powder present in an amount defining a powder initiator fraction,
    b) a liquid component comprising i) an acrylic monomer and ii) an accelerator present in an amount defining a liquid accelerator fraction,
  wherein a portion of the acrylic polymer powder comprises an anti-oxidant,
  wherein the acrylic polymer powder comprises
  a first fraction having a particle size less than 5 um; a second fraction having a particle size between 5 um and 20 microns and comprising the anti-oxidant; and a third fraction having a particle size greater than 20 microns.

2. The formulation of claim 1 wherein the acrylic polymer powder comprises PMMA.

3. A bone cement formulation comprising:
    a) a powder component comprising: i) an acrylic polymer powder, and ii) an initiator powder present in an amount defining a powder initiator fraction,
    b) a liquid component comprising i) an acrylic monomer and ii) an accelerator present in an amount defining a liquid accelerator fraction,
  wherein a portion of the acrylic polymer powder comprises an anti-oxidant,
  wherein the acrylic polymer powder comprises
  a first fraction having a molecular weight less than 500,000 kDa; a second fraction having a molecular weight between 500,000 and 600,000 k D and comprising the anti-oxidant; and a third fraction having a molecular weight greater than 600,000 kDa.

4. A bone cement formulation comprising:
    a) a powder component comprising: i) an acrylic polymer powder, and ii) an initiator powder present in an amount defining a powder initiator fraction,
    b) a liquid component comprising i) an acrylic monomer and ii) an accelerator present in an amount defining a liquid accelerator fraction,
  wherein a portion of the acrylic polymer powder comprises an anti-oxidant,
  wherein the acrylic polymer powder comprises
  a first fraction having a molecular weight less than 500,000 kDa; a second fraction having a molecular weight between 500,000 and 600,000 k D and comprising the anti-oxidant and a third fraction having a molecular weight greater than 600,000 kDa, and
  wherein the first fraction comprises between 60-90 wt % of the powder component; the second fraction comprises about 1 wt % of the powder component; and the third fraction comprises between 1 and 4 wt % of the powder component.

5. The formulation of claim 1 wherein the acrylic polymer powder comprises at least 50 wt % of the powder component.

6. The formulation of claim 1 wherein the anti-oxidant comprises between 0.01 mol % and 1 mol % of the acrylic polymer powder.

7. The formulation of claim 1 wherein the anti-oxidant is a polyphenol.

8. The formulation of claim 1 wherein the powder component further comprises iii) between 5 wt % and 35 wt % contrast agent powder.

9. The formulation of claim 1 wherein the powder component further comprises iii) between 25 wt % and 35 wt % contrast agent powder.

10. A bone cement formulation comprising:
    a) a powder component comprising i) an acrylic polymer powder, ii) an initiator powder present in an amount defining a powder initiator fraction, and iii) a carrier powder comprising a delayed-release polymerization inhibitor;
    b) a liquid component comprising i) an acrylic monomer and ii) an accelerator present in an amount defining a liquid accelerator fraction,
  wherein the carrier powder comprising a delayed-release polymerization inhibitor has a coating thereon.

11. The formulation of claim 10 wherein the delayed-release polymerization inhibitor is dispersed within the carrier powder.

12. The formulation of claim 10 wherein the coating is an acrylic coating.

13. A bone cement formulation comprising:
    a) a powder component comprising i) an acrylic polymer powder, ii) an initiator powder present in an amount defining a powder initiator fraction, and iii) a carrier powder comprising a delayed-release polymerization inhibitor;
    b) a liquid component comprising i) an acrylic monomer and ii) an accelerator present in an amount defining a liquid accelerator fraction,
  wherein the delayed-release polymerization inhibitor is contained in a shell.

14. The formulation of claim 13 wherein the shell is selected from the group consisting of a microbubble, a micelle and a liposome.

15. The formulation of claim 10 wherein the delayed-release polymerization inhibitor is an anti-oxidant.

16. The formulation of claim 10 wherein the delayed-release polymerization inhibitor is a free radical scavenger.

17. The formulation of claim 10 wherein the delayed-release polymerization inhibitor is a phenolic compound.

18. The formulation of claim 10 wherein the delayed-release polymerization inhibitor is hydroquinone.

19. The formulation of claim 10 wherein the delayed-release polymerization inhibitor is a polyphenol.

* * * * *